United States Patent [19]

Sandhu

[11] 4,348,206
[45] Sep. 7, 1982

[54] SLURRY PIPELINE SIMULATION METHOD

[75] Inventor: Avtar S. Sandhu, Tiburon, Calif.

[73] Assignee: Bechtel International Corporation, San Francisco, Calif.

[21] Appl. No.: 203,775

[22] Filed: Nov. 3, 1980

[51] Int. Cl.³ .................... G01N 33/22; G01N 33/24
[52] U.S. Cl. .............................. 23/230 A; 73/432 SD
[58] Field of Search ................ 23/230 A; 73/432 SD; 366/54, 56, 62, 63, 142, 220; 162/357

[56] References Cited

U.S. PATENT DOCUMENTS 2,347,357 4/1944 Mason ............................ 366/220 X
3,201,309 8/1965 Stuebe et al. ........................ 162/357

Primary Examiner—Richard V. Fisher
Attorney, Agent, or Firm—Townsend and Townsend

[57] ABSTRACT

Method for simulating the effect upon liquid properties after the passage of a slurry composed of a mixture of solid particulates and liquid through a length of pipeline uses for simulation an apparatus including an outer cylinder closed at both ends. The outer cylinder is horizontally mounted for rotation about its axis and includes a removable cap. Mounted coaxially within the outer cylinder is a relatively small diameter cylindrical pipe. The outer cylinder is made of a material which is substantially inert with respect to a slurry. The outer surface of the cylindrical pipe corresponds to the material for which the actual pipeline is designed. The outer cylinder and the cylindrical pipe are sized so that by rotating the outer cylinder, with a test slurry located between the cylindrical pipe and outer cylinder, for a predetermined time at a chosen speed, the properties of the water in the slurry after passage through the pipeline is simulated.

10 Claims, 4 Drawing Figures

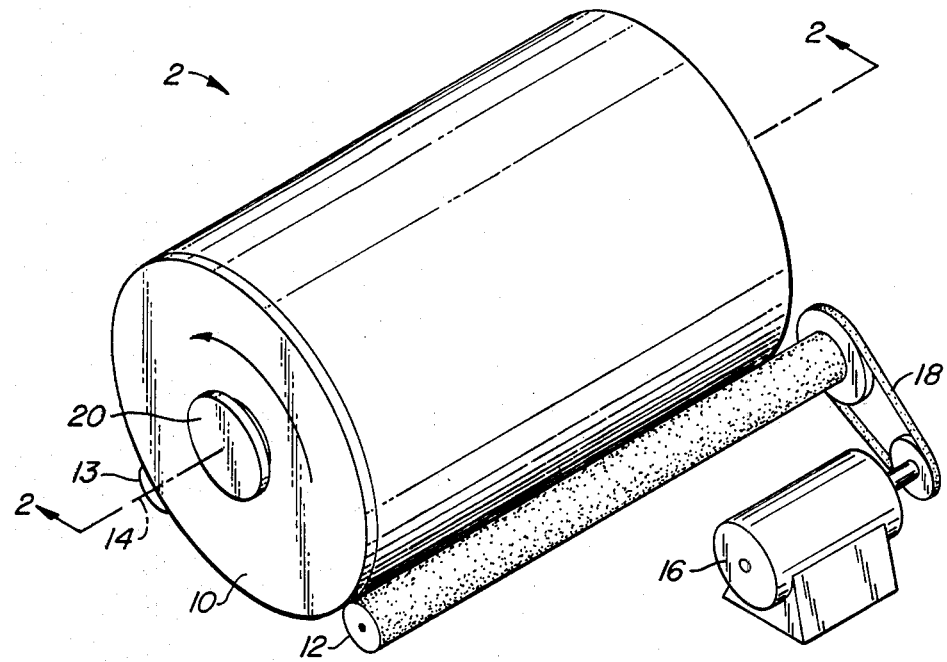
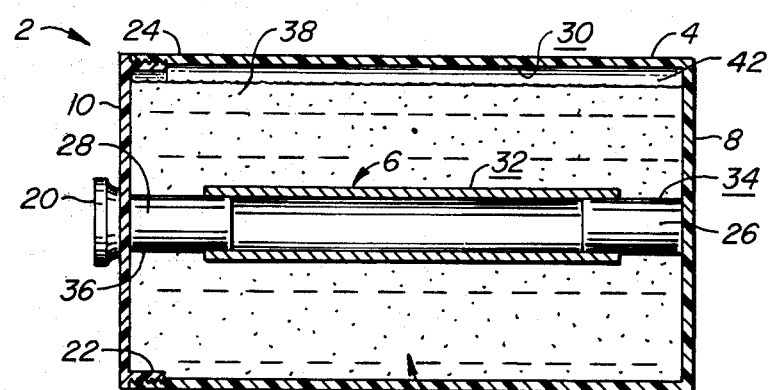
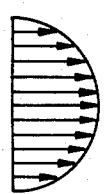
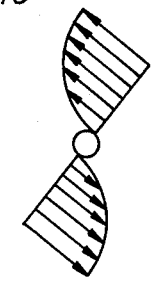

SLURRY PIPELINE SIMULATION METHOD

BACKGROUND OF THE INVENTION

Slurry pipelining is the transportation of a mixture of crushed solid particles and liquid within a pipeline. The slurry is usually pumped because of the contour and length of the pipeline and the friction of the slurry against the pipeline interior.

During transportation, the solid particles, such as iron ore and coal, may be leached by and mixed chemically with the liquid, usually water. Also, very small particles, known as fines, may be created which mix physically with the liquid.

At the discharge end of the pipeline, the particles are separated from the liquid in a dewatering-type process so that they will be usable. The liquid must then be disposed of by discharge as waste, treated for further use, or returned to the point of origin for reuse. It is generally too expensive to return the liquid to the point of origin for reuse or to treat it for human or commercial uses. Therefore the liquid is usually disposed of as waste or for irrigation.

Current environmental regulations require that before the liquid, such as water, can be disposed of locally, it must be treated to meet certain quality standards. For this reason, it is imperative to know whether the liquid can be treated to meet these standards before a major pipeline is built. This requires knowing what changes, if any, the solids being transported will have upon the liquid, so as to know whether the liquid can be successfully and economically treated to meet those standards.

This invention simulates the effects, if any, of the transportation of solids on the liquid so that the required treatment can be determined.

SUMMARY OF THE INVENTION

The present invention allows the simulation of the effects of the solid particles upon a liquid caused by the travel of a slurry through a pipeline. As the liquid is usually water and the solid particles are often coal, water and coal will be used below to describe the invention but not to limit either the liquid or solid particles that can be transported within the pipeline.

The laboratory test apparatus used to produce the effects, if any, of the solid particles upon the liquid in a slurry pipeline includes an outer cylinder closed at both ends. The outer cylinder is horizontally mounted for rotation about its axis and includes a cap at one end for introduction of the slurry within the cylinder. Mounted coaxially within the outer cylinder is a cylindrical pipe, the diameter of which is substantially less than the diameter of the outer cylinder. The outer cylinder is made of a material which is substantially inert with respect to the slurry. The outer surface of the pipe corresponds to the material for which the interior of the contemplated pipeline is designed. The outer cylinder and the cylindrical pipe are sized so that rotating the horizontally disposed outer cylinder, the slurry being located between the cylindrical pipe and the outer cylinder, for a predetermined time at a chosen speed simulates the effects, if any, of the material upon the liquid during the transport of the slurry through the pipeline.

To determine the changes in water quality, i.e. what elements, chemicals and other matter are in the water and in what quantities, as a result of pumping a coal/water slurry through a pipeline, several aspects are simulated. First, the inertial forces of the particles of the slurry to be transported in the pipeline and of the particles of the slurry to be used in the apparatus are the same. Secondly, the velocity profile of the pipeline and the apparatus are the same. Thirdly, the exposure of the pipeline slurry to the interior surface of the pipeline is simulated in the apparatus by installing the appropriate material, such as steel, within the cylinder so that it contacts the slurry therein.

In the inertial forces simulation, it is shown below that the time factor of the slurry within the pipeline is equal to the square root of the particle size factor. Therefore, by choosing the same size particles for the test slurry as are used in the pipeline slurry, a one-to-one time scale results. Since the particles used are of the same material, inertial forces are simulated on the one-to-one scale.

In an operational pipeline, the pipeline is stationary while the slurry inside moves at a specified velocity in the turbulent flow regime. In the laboratory test apparatus, the container is in rotational motion while the slurry is under inertial turbulence due to velocity shear at the wall of the outer cylinder. It should be noted that the maximum velocity, corresponding to the velocity at the center of the pipeline, occurs in the apparatus at the surface of the outer cylinder and the minimum velocity occurs next to the cylindrical pipe mounted along the axis of the outer cylinder. Since the maximum velocity at the center of the pipeline is to be duplicated at the surface of the outer cylinder, for a chosen diameter of the outer cylinder, a corresponding rotational speed will duplicate that velocity. However, the values for the diameter of the cylinder and the speed of rotation must be checked so that the centrifugal force produced by the rotational movement is not greater than the force due to gravity. If this occurred, the particles would be forced against the surface of the cylinder and turbulence would be lost. By judicious selection, turbulence can be simulated.

By simulating the inertial forces and the velocity profile of the pipeline, the effect of the coal particles upon the water can be determined. For example, coal does not dissolve in water but certain chemical compounds, such as sodium chloride and potassium sulfate, may be leached from the coal by the water while the slurry is being pumped through the pipeline.

Further, the effect of the contact of the slurry with the inside surface of the operational pipeline must also be simulated. To do so the circular pipe is mounted along the axis of the cylinder. By equating the pipeline surface area-to-volume with the test apparatus surface area-to-volume, an appropriate size (length and diameter) for the circular pipe within the cylinder can be determined.

Other features and advantages of the present invention will appear from the following description in which the preferred embodiment has been set forth in detail in conjunction with the accompanying drawings.

BRIEF DESCRIPTION OF THE DRAWINGS

FIG. 1 is an isometric view of the apparatus of the invention.

FIG. 2 is a cross-sectional view of the cylinder.

FIG. 3 is a representation of the net velocity profile across the pipeline.

FIG. 4 represents the net velocity profile in the test apparatus.

DETAILED DESCRIPTION OF THE PREFERRED EMBODIMENT

Turning now to FIGS. 1 and 2, the slurry pipeline simulation test apparatus 2 includes generally an outer cylindrical container or drum 4 having a pipe 6 therein mounted between end 8 and cap 10 of the drum. The drum is mounted horizontally on rollers 12, 13 and is rotated about its longitudinal axis 14 by motor 16. The motor drives a belt 18 which is passed around a pulley at one end of roller 12.

The cap 10 has a handle 20 for removal. Cap 10 has an internally directed flange 22 for threadable engagement with open end 24 of the drum. Rods 26 and 28 are fastened to the center of end 8 and cap 10 and extend inwardly within the drum. The rods are sized so that pipe 6 forms a press fit over the outer surfaces of the rods. The interior of the drum between inside surface 30 of the drum and outside surface 32 of the pipe and the exposed surfaces 34, 36 of rods 26, 28 define an interior chamber 38. Chamber 38 is substantially filled with a test slurry 40. The test slurry is a mixture of the test liquid, typically water, and a test particulate such as crushed coal. Usually, a small space 42 is provided and filled with nitrogen to produce a discontinuity in the rotation pattern of the slurry. This discontinuity is so that the desired turbulence of the slurry can be maintained.

Having now described the structure of the invention, attention now will be directed to the computational analysis used in designing and operating the apparatus with the test slurry inside to simulate the pipeline conditions under which slurry is transported through the pipeline.

In order to determine the effect of the coal upon the water during their transportation as slurry within a pipeline, the following takes place:

Inertial Forces Simulation

Inertial forces are simulated so that during movement of the slurry, the test (or model) particles and the pipeline particles react similarly.

$$F(inertia) = m \cdot a = \rho \cdot l^3 \cdot a,$$

where:
F(inertia) = the inertia force of the particle,
m = mass,
a = acceleration,
p = mass density, and
l³ = volume.

$$\text{Defining: } I = \frac{\rho(m) \cdot l(m)^3 \cdot a(m)}{\rho(p) \cdot l(p)^3 \cdot a(p)},$$

where:
I = a dimensionless inertia force factor,
ρ(m) and ρ(p) are the mass densities of the test (or model) and the pipeline particles,
l(m)³ and l(p)³ are volumetric representations of the test and the pipeline particles in terms of length (l) scales, and
a(m) and a(p) are the particle accelerations for the test and the pipeline.
Letting $L = [l(m)/l(p)] =$ length scale factor, and substituting $\gamma/g$ for $\rho$,
where:

γ is the weight density and
g is the acceleration due to gravity, we get $$I = \frac{\gamma(m) \cdot g(p)}{\gamma(p) \cdot g(m)} \cdot L^3 \frac{a(m)}{a(p)}.$$

Expressing a(m) and a(p) in terms of distance units (α(m) and Δ(p)) per unit time squared (t(m)² and t(p)²), we have:

$$I = \frac{\gamma(m) \cdot g(p)}{\gamma(p) \cdot g(m)} \cdot L^3 \cdot \frac{\Delta(m) \, t(p)^2}{\Delta(p) \, t(m)^2}.$$

Letting $[t(m)/t(p)] = T =$ time factor, we have $$I = \frac{\gamma(m) \cdot g(p)}{\gamma(p) \cdot g(m)} \cdot L^3 \cdot \frac{\Delta(m)}{\Delta(p)} T^{-2}. \quad (1)$$

In order to simplify equation (1) above, we note that a gravitational factor G, defined as $g(m) \div g(p)$, can be expressed in terms of units as:

$$G = \frac{g(m)}{g(p)} = \frac{l(m) \cdot t(p)^2}{l(p) \cdot t(m)^2} = LT^{-2}.$$

Assuming that gravity is the same for the test (or model) and pipeline slurries, we get:

$$G = \frac{g(m)}{g(p)} = 1, \text{ so that} \quad (2)$$

$$T = \sqrt{L}.$$

By the judicious choice of the same slurry (same size range of particles, same densities, etc.) for the test simulation and the pipeline, the following relationships result:
l(m) = l(p), which by definition yields
L = 1.0.
Substituting this result in equation (b 2) we have:

T = 1.
With the above factors, L, T and G are all equal to 1, equation (1) reduces to:

$$I = \frac{\gamma(m) \cdot \Delta(m)}{\gamma(p) \cdot \Delta(p)}.$$

Recognizing that the weight densities for the slurries are equal makes, $$\frac{\gamma(m)}{\gamma(p)} = 1.0.$$

Recognizing that for the purposes of this dimensional similitude analysis, $$\frac{\Delta(m)}{\Delta(p)} = 1, \text{ we have}$$

$$I = 1.0.$$

Therefore, inertia forces are simulated on a 1:1 scale.

Velocity Simulation

The maximum velocity and velocity profile over the cross-section of the pipeline is simulated in an unusual manner. In the pipeline, the maximum velocity occurs in the center of the pipeline while the minimum velocity occurs along the inside surface of the pipeline. A cross-sectional representation of the velocity profile of the pipeline is shown in FIG. 3. In the simulation test apparatus, the velocity profile, as represented in FIG. 4, is at its maximum along the inside surface of the drum and is at its minimum next to the cylindrical pipe mounted along the axis of the drum. By equating the maximum velocity at the center of the pipeline to the maximum tangential velocity of the drum, velocity simulation is achieved. The profile of FIG. 4 is essentially that of FIG. 3 divided in half and placed generally end-to-end.

It should be noted that in the preferred embodiment, pipe 6 is not stationary but rotates along with the drum. If desired, pipe 6 could be maintained stationary while drum 4 was rotated. This would more closely model the pipeline in that the inner surface of the pipeline which pipe 6 simulates is stationary. However, because of the relatively small diameter of the pipe, the tangential velocity of the pipe at its surface 32 is small so that reasonable simulation is achieved even though pipe 6 is rotated along with drum 4. The radius of the drum and speed of rotation of the drum are determined according to the following equations.

Setting $V(m) = V(p) =$ maximum tangential velocity of the apparatus equal to the maximum (center) velocity of pipeline, we have, $$V(p) = V(m) = R \cdot \omega,$$

where:

$R$ = radius of inside surface 30 of drum 4, and $\omega$ = angular velocity of the drum in radians per second.

However, R and $\omega$ must be chosen so that the centrifugal forces on the particles do not exceed the gravitational forces to insure turbulence simulation is achieved. This is true so long as $g > R \cdot \omega^2$, where g is the acceleration due to gravity.

As the drum is rotated, especially when rotated at a constant velocity, there may be a tendency for the slurry immediately adjacent to the drum to cease moving relative to the drum. Space 42 provides a discontinuity so that the particles near the inside surface are deflected into a new direction of travel as they contact the space. This is so that a degree of relative motion between the particles in the slurry and the drum is maintained. Thus, the necessary turbulence is maintained within the rotating drum to the desired level. Space 42 is preferably filled with an inert gas, such as nitrogen, to avoid chemical changes in the slurry which may otherwise be introduced.

Steel Pipe Simulation

In the analysis above, the simulation of the inertial forces upon the particles, the velocity profile, and the assurance of turbulent motion has been discussed. In this simulation, revolving the drum about its horizontally disposed axis will cause the particles in the slurry to move about within the drum in a manner similar to being pumped through the pipeline. Therefore, changes in the slurry, such as compounds being leached from the coal into the water, will be duplicated. However, the slurry also comes in contact with the interior surface of the pipeline so that the interaction of the slurry and the pipeline, and its effect upon the slurry, must also be simulated.

One fact which must be remembered is that the velocity of the slurry adjacent to the walls of the pipeline is generally quite low. To accurately stimulate the pipeline/slurry interaction, that which simulates the pipeline surface should also contact the slurry in a region where the velocity of the slurry is low. This occurs along the center of the drum. In the preferred embodiment, a cylindrical pipe is mounted along the axis of the drum. To obtain simulation of the pipeline surface, pipe 6 is chosen with an exposed surface area per unit volume of test slurry 40 ratio equal to the surface to volume ratio of the pipeline. The following calculations detail this procedure.

Letting:

$Rp$ = Internal radius of the pipeline,
$Lp$ = Length of the pipeline,
$L$ = Length of drum 4,
$r$ = Radius of pipe 6,
$l$ = Length of pipe 6,
$\Delta(v)$ = Volume of space 42, we have, $$\frac{\text{Surface area of pipeline}}{\text{Volume of pipeline}} = \frac{\text{Exposed surface area of pipe 6}}{\text{Volume of test slurry 40}}$$

Substituting we get:

$$\frac{2\pi \cdot Rp \cdot Lp}{\pi \cdot Rp^2 \cdot Lp} = \frac{2\pi \cdot r \cdot l}{[\pi \cdot L \cdot (R^2 - r^2)] - \Delta(v)},$$

simplifing $$[\pi \cdot L \cdot (R^2 - r^2)] - \Delta(v) = \pi \cdot r \cdot l \cdot Rp.$$

Therefore, L, r and R are chosen in accordance with the above relationship. In doing so, it is advisable to keep r relatively small compared with R so that the tangential velocity of pipe 6 is small.

It should be noted that the material choice for drum 4 should be substantially inert with respect to the slurry.

In the preferred embodiment the sample slurry is chosen to be similar to the slurry pumped through the pipe-line. This is achieved by producing a test particulate meeting the same particle size specifications as the pipeline particulate. This, as can be seen from the above analysis, simplifies the relationships and helps to obtain reliable test data. However, if desired, a test slurry different from the pipeline slurry could be used; appropriate changes in the relationships used would then be made.

If desired, other configurations for the pipe similation surface could be used. For example, a center rod mounted along the axis of drum 4 and having a number of radially extending disks could be used. Once again, care must be taken so that the tangential velocity along the surface of the disks are relatively small compared to the velocity of drum 4. Using disks would allow the surface area-to-volume ratio to more easily be obtained.

Although the preferred mode contemplated for carrying out the present invention has been herein shown and described, modification and variation may be made without departing from what is regarded to be the subject of the invention.

What is claimed is:

1. A method for simulating the effect upon a first slurry, comprising a mixture of solid particulates and a liquid, after it has passed through a pipeline, comprising the following steps:

providing a test slurry comprising a test liquid and test solid particulates;

providing a closed, horizontally disposed drum, said drum having a circular cross-sectional shape, an inside surface and mounted for rotation about its axis, a pipeline simulation surface mounted within and generally along the axis of said drum, and door means for introducing said test slurry within said drum;

adding said test slurry to said drum;

rotating said drum for a predetermined time; and analyzing said test slurry after being rotated whereby the expected effect upon said first slurry after passing through said pipeline is determined.

2. The method according to claim 1 wherein said test slurry is a coal-water slurry.

3. The method according to claim 1 wherein said rotating step is executed on a constant basis.

4. The method according to claim 1 wherein said test particulate is similar to said particulate in the first slurry.

5. The method of claim 1 wherein said predetermined time is proportional to the square root of the ratio of the size of the test particulate to the size of the said particulate in the first slurry.

6. The method according to claim 1 wherein said first slurry and said test slurry are of substantially the same composition.

7. The method according to claim 1 wherein said drum is cylindrical and is rotated at a predetermined speed, said predetermined speed determined by the following relationship:

$$R \cdot \omega = V(p),$$

where:
  $R$ = radius of said drum to said inside surface,
  $\omega$ = said predetermined speed in radians per units of time, and
  $V(p)$ = velocity of said first slurry at the center of said pipeline.

8. The method according to claim 7 wherein said relationship is further determined by the following relationship:

$$R \cdot \omega^2 < g,$$

where: $g$ = acceleration due to gravity.

9. The method according to claim 1 wherein said test slurry in said drum incompletely fills said drum to leave a space between said test slurry and a portion of said inside surface so as to maintain turbulence in said test slurry.

10. The method according to claim 9 wherein said space is filled with nitrogen.

* * * * *